United States Patent [19]

Falk

[11] Patent Number: 4,535,640
[45] Date of Patent: Aug. 20, 1985

[54] CERAMIC FIBER MOLTEN METAL SAMPLER

[76] Inventor: Richard A. Falk, 519 Westminster Dr., Waukesha, Wis. 53186

[21] Appl. No.: 547,930

[22] Filed: Nov. 2, 1983

[51] Int. Cl.³ ............................................. G01N 1/12
[52] U.S. Cl. ................................. 73/864.55; 264/219
[58] Field of Search ......... 73/DIG. 9, 864.52, 864.53, 73/864.54, 864.55, 864.56, 864.57, 864.58, 864.59; 374/139, 140, 157; 264/219, 225, 226; 164/6, 15, 37, 44

[56] References Cited

U.S. PATENT DOCUMENTS

| | | | |
|---|---|---|---|
| 3,559,452 | 2/1971 | Perbix et al. | 73/864.55 |
| 3,994,172 | 11/1976 | Kelsey | 73/864.55 |
| 4,007,641 | 2/1977 | Kelsey | 73/DIG. 9 |
| 4,468,009 | 8/1984 | Clauss | 374/140 |

Primary Examiner—S. Clement Swisher
Attorney, Agent, or Firm—Fuller, House & Hohenfeldt, S.C.

[57] ABSTRACT

A non-splash molten metal sampler has a refractory fiber body which defines a cylindrical mold cavity with sand-resin plugs providing end walls for the cavity. The plugs can be formed in place. The fiber body is easily machined to provide a side entry port and grooves for pin sample tubes and thermocouple wires.

8 Claims, 5 Drawing Figures

U.S. Patent        Aug. 20, 1985        4,535,640
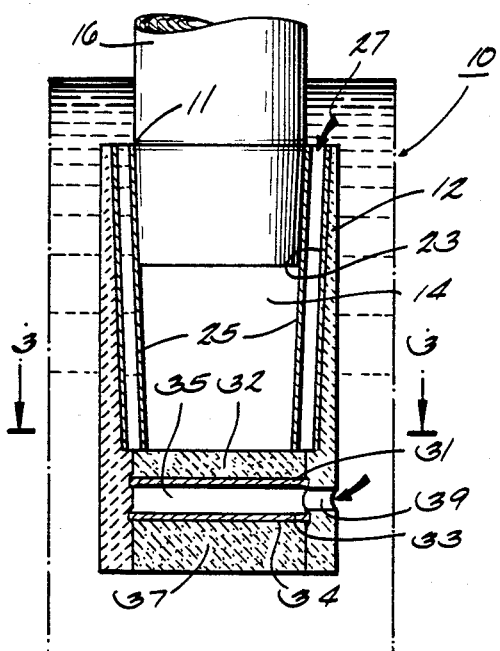
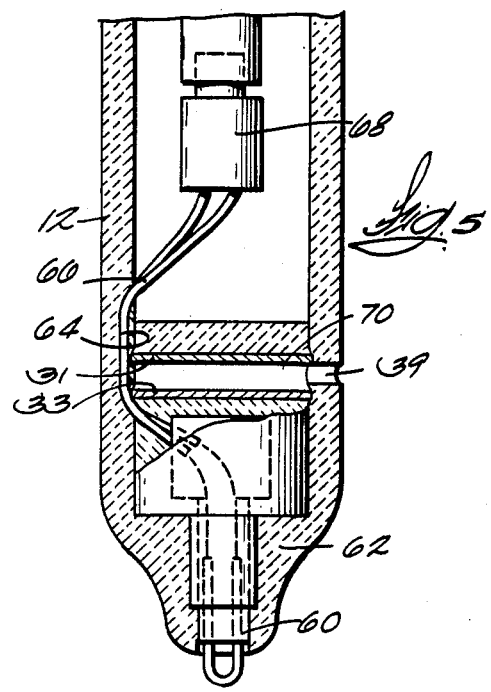

CERAMIC FIBER MOLTEN METAL SAMPLER

FIELD OF THE INVENTION

The invention relates to molten metal sampling equipment.

BACKGROUND OF THE INVENTION

In some types of molten metal sampling, metal splash is a risk to the tester and can cause a problem with associated test equipment. Typically ceramic or metal molds are employed in a wide range of metal sampling. These materials cause a more rapid chill, and with low temperature metal can result in solidification of the metal before the mold is completely filled.

SUMMARY OF THE INVENTION

The invention provides a non-splash metal sampler made of refractory fiber which minimizes the chill to the sample and provides the advantages not found with the ceramic and complete metal mold halves. The use of a refractory fiber such as Babcock & Wilcox's Kaowool 2600 bulk fiber, which is 55% alumina and 44.9% silica can be employed. This fiber enables easy machining or forming so that grooves can be put in the side walls of the sampler cartridges for pin sample tubes or for electrical wires to connect with a bath temperature measuring thermocouple. The refractory fiber body can be either formed in one tubular unit, or it can be formed in two split halves which are secured together in a generally cylindrical shape with refractory cement along the split line. Molded sand-resin plugs for the ends of the sample cavity can either be injected through an opening in the mold cavity or pre-formed.

Further objects, features and advantages of the invention will become apparent from the disclosure.

DESCRIPTION OF THE DRAWINGS

FIG. 1 is a side elevational view in fragmentary section of one embodiment of the invention;

FIG. 2 is a view similar to FIG. 1 with the parts exploded;

FIG. 3 is a sectional view along lines 3—3 of FIG. 1;

FIG. 4 is a fragmentary sectional view of a modified embodiment of the invention; and FIG. 5 is a fragmentary sectional view of a sampler and a bath temperature sensor.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structure. The scope of the invention is defined in the claims appended hereto.

FIG. 1 shows a sampler 10 in which the first wall means 12 defines a cylindrical cavity 14 which receives a handle or short paperboard tube 16 for manipulating and immersing the sampler 10 in molten metal. The first wall means can be formed from a single sleeve or two split sleeves 12 (FIG. 2) joined together by refractory cement 18, as illustrated in FIG. 3. The first wall means is made of a refractory or ceramic heat resistant fiber. Kaowool is suitable for this purpose. The inside surface 21 of the wall 12 is provided with grooves or recesses 23 (FIGS. 2 and 3) which are inclined inwardly to receive and position the pin sample tubes 25. The pin sample tubes 25 are retained in the grooves by the tube 16. The tubes 25, 12 fill from the top, as shown by the arrow 27.

The sampler illustrated in FIG. 1 also includes second wall means 32 and 34 and steel or other smooth plates 31, 33. The wall means 32 can be formed in place by pouring the sand mix for wall 32 in from the open end 11 of the sampler and onto plate 31 or a pre-formed disc 32 can be employed and inserted against a steel plate 31 which forms a top wall of the sample cavity 35 and forms smooth flat surfaces on the sample 38 (FIG. 2). Alternatively, the sand mix can be injected in a small aperture 51 after the discs or plates 31 are pressed into the interior wall of the sampler. The wall or plug 34 can be formed in place with the same mix beneath a plate 37 which forms the bottom of the mold cavity 35. The fill hole or aperture 39 is easily punched, drilled or formed in plate after the parts are assembled. The discs 31, 33 can be pressed into place in the relatively soft fiber walls.

FIG. 4 illustrates a modified embodiment in which the first wall means 42 is formed with an integral shoulder 44 and a smaller diameter zone 46 located between upper and lower chill plates 48 and 50 which define the top and bottom of the sample cavity 52. The plates 48 and 50 provide smooth surfaces on the disc to facilitate and minimize machining prior to spectrographic analysis.

A fused quartz fill tube 54 located in a recess 56 in the wall means 42 communicates directly with the fill passage 58 for bottom filling rather than top filling as illustrated in the FIG. 1 embodiment.

Referring to FIG. 5, a modified embodiment is illustrated which includes a bath temperature heat sensor assembly 60 supported by a molded nose part 62 for the first wall means. The first wall means is grooved at 64 to enable the wires 66 from the connector head 68 to bypass the fill chamber or mold sample cavity 70.

With all embodiments, the loose sand-resin mix if employed is baked in place after assembly of the samples. Refractory fiber does not gas or boil when immersed in molten metal as do the paperboard tubes typically employed as a holder and carrier for molten metal samplers.

The discs 31, 33 are pressed into the soft walls of the split sleeves 12 and retained in place by the press-formed grooves 79 in the sleeves 12, FIG. 5. This greatly facilitates assembly.

I claim:

1. A molten metal sampler comprising first wall means defining a generally cylindrical sample cavity, said first wall means being formed from temperature resistant fibers, and second wall means for sealing the ends of said sample cavity, said second wall means comprising molded sand-resin plugs spanning said cavity, said plugs being in sealing contact with said first wall means and a side entry port to introduce molten metal between said plugs, and smooth plates between said sand plugs and spaced to form disc samples with smooth surfaces.

2. A sampler in accordance with claim 1 in which the sand plugs are molded in place by inserting sand-resin mix through the aperture in said first wall means.

3. A sampler in accordance with claim 1 including pin sample tubes inserted in grooves in said first wall means which extend angularly inwardly from the top of said first wall means toward said second wall means, said fill tubes being positioned in recesses in said first wall means to provide clearance for a mounting tube, and a tube which is inserted in said first wall means and which tube holds said pin sample tubes in place.

4. A sampler in accordance with claim 1 in which said first wall means is formed by two split wall means formed from refractory fiber which are cemented together by refractory cement along the juncture of the wall means.

5. A sampler in accordance with claim 1 in which said first wall means is provided with a shoulder to support one of said metal discs of a larger diameter than the other disc.

6. The sampler of claim 1 including recesses formed in said first wall means for electrical wires to supply a thermocouple head at one end of said sampler.

7. A sampler in accordance with claim 1 including a recess in the interior side wall of said sampler, said recess intersecting said side fill opening, and a pin sample tube in said recess communicating with said side fill opening to receive molten metal therefrom.

8. A method of making a molten metal sampler comprising the steps of providing a cylindrical mold body formed from refractory fibers having a mold cavity formed from refractory fiber, providing discs to define walls of the mold cavity, forming a hole in the mold body and injecting a sand-resin mix against a disc to form an end wall for the sample cavity.

* * * * *